United States Patent [19]

de Yampert et al.

[11] 4,329,997

[45] May 18, 1982

[54] COLD/HOT COMPRESSION AND ELEVATION APPARATUS

[76] Inventors: H. Donn de Yampert, 3216 Hamilton, El Paso, Tex. 79930; Sergio Renteria, 4504 Avenue A., Austin, Tex. 78751

[21] Appl. No.: 152,738

[22] Filed: May 23, 1980

[51] Int. Cl.³ .............................................. A61F 7/00
[52] U.S. Cl. .................................................. 128/402
[58] Field of Search ............... 128/402, 399, 82.1, 128/89, 379, 382, 400

[56] References Cited

U.S. PATENT DOCUMENTS

| | | | |
|---|---|---|---|
| 1,775,442 | 9/1930 | Sarason | 128/402 |
| 2,702,552 | 2/1955 | Moodie | 128/375 |
| 3,548,819 | 12/1970 | Davis et al. | 128/402 |
| 3,561,435 | 2/1971 | Nicholson | 128/82.1 |
| 3,678,936 | 7/1972 | McCormick | 128/402 |
| 4,071,031 | 1/1978 | Lowman | 128/402 |
| 4,149,529 | 4/1979 | Copeland et al. | 128/402 X |

FOREIGN PATENT DOCUMENTS 1491215  7/1970  Fed. Rep. of Germany ........ 128/89

*Primary Examiner*—John D. Yasko
*Attorney, Agent, or Firm*—Saidman & Sterne

[57] ABSTRACT

Compression and elevation apparatus particularly designed for use by an athlete immediately after sustaining a soft-tissue injury, and which also may be used during subsequent treatment of the injury. The apparatus comprises a substantially rectangular tank having a pair of apertures on opposed, parallel sides thereof, one aperture being positioned higher than the other. A waterproof, flexible tubing, such as rubber, is connected between the apertures and is adapted to receive the injured arm or leg. Immediately after sustaining an injury, the user inserts his injured limb through the tube and the tank is filled with a mixture of water and ice, which results in immediate cold compression on the injured limb while being maintained in an elevated position. During subsequent treatment, the tank may be filled with hot water to provide heat treatment for the limb, or two tanks, one having hot water and one having cold water, may be used for contrast therapy.

6 Claims, 2 Drawing Figures

COLD/HOT COMPRESSION AND ELEVATION APPARATUS

BACKGROUND OF THE INVENTION

1. Field of the Invention

The present invention is related to devices for treating injured limbs and, more particularly, is directed toward a portable apparatus which is designed to provide cold compression on an elevated, injured limb as soon as possible after the injury, and which also may be used during subsequent treatment for application of heat or in contrast therapy.

2. Description of the Prior Art

Various devices have been proposed in the past for treating injured limbs. Such devices are exemplified by the following U.S. Pat. Nos.: 1,775,442; 2,702,552; 3,561,435; 3,678,936; 4,071,031; and 4,149,529.

While each of the devices described in the above-cited patents may be useful under special circumstances, I have found that, when utilized to treat soft-tissue injuries to the arm or leg of an athlete, each of the patented devices suffers from one or more deficiencies. For example, the device described in U.S. Pat. No. 4,071,031 comprises a limb support which is designed to elevate the limb of the patient and which is also adapted to receive fluid or ice for treating the injured limb. This device is remiss in that it fails to provide any means for compressing the injured tissue, which can be extremely important in reducing the healing time of the injury. Other devices, such as those described in U.S. Pat. Nos. 1,775,442 and 2,702,552, place the injured or treated limb in direct contact with the treatment fluid, which can undesirably affect the wound.

In dealing with athletic injuries, we have discovered that it is extremely important to be able to treat the injured limb as soon as possible after the injury has occurred. Therefore, an important feature of a practical limb-treatment device for athletes would be its simplicity and portability so that it can be available on the playing field when needed.

Another important design feature for a practical limb-treatment device for athletes would be that the injured limb be compressed. This can be especially important if the injury involves internal bleeding, since such compression will assist in limiting the amount of or stopping the internal bleeding. Another feature of such a device should be that it offers elevation to the injured limb which, together with the compression, delays swelling. The overall effect of such a device would be to substantially reduce the recovery time of the athlete from that heretofore necessary. For mass production, the device should also be as simple in construction as possible, and be made of readily available components.

The importance of immediate application of cold to a sports-related injury has been confirmed by articles such as "Athletic Injuries: Heat vs. Cold", A. Kalenak, MD., et al, *AFP*, November 1975, pp. 131-134, Vol. 12. No. 5, and "Rehabilitating the Injured Athlete", V. Smodlaka, MD, ScD, *The Physician and Sportsmedicine*, Vol. 5, No. 11, November 1977. The latter article also recognizes the need for compression and elevation of the injured extremity.

It is also known that it may be desirable to apply heat to the injury some 2-3 days after the injury occurs. Heat therapy accelerates the process of repair by stimulating local circulation and preventing fibrosis with early active exercise. Contrast treatment involves the alternate submission of the injured extremity in hot and cold water, and has also been shown to the beneficial. See, for example, "Contrast Bath Treatment for Sprains" by Gary K. Smith, *The Physician and Sports Medicine*, March 1967, p. 133.

The present invention is advanced with a view toward meeting the above-noted requirements for a practical limb-treatment device for athletes while overcoming the deficiencies of the prior art devices described above.

OBJECTS OF THE INVENTION

It is therefore a primary object of the present invention to provide a device for treating injured limbs of athletes which overcomes all of the deficiencies noted above with respect to prior art devices.

Another object of the present invention is to provide a device for treating soft-tissue injuries on a leg or arm which is of simple construction, readily portable, may be assembled from available components, is inexpensive to produce, and the use of which will greatly reduce the time between the onset of the injury and the treatment thereof to thereby reduce recovery time.

A still further object of the present invention is to provide a device for permitting immediate treatment of a leg or arm injury of an athlete which is capable of providing simultaneous ice compression and elevation of the injured limb to assist in stopping the bleeding and delay swelling of the injured limb.

Another object of the present invention is to provide a device which may be used either for hot or cold therapy for treatment of injury to limbs.

SUMMARY OF THE INVENTION

The foregoing and other objects are attained in accordance with one aspect of the present invention through the provision of a device for treating an injured body limb, which comprises a tank adapted to contain a treatment fluid such as ice water or hot water and which includes first and second opposed end walls, and tubular means connected to and extending between the end walls of the tank for encircling and compressing the injured limb within the fluid contained in the tank, the tubular means comprising a liquid-impervious, flexible tube having an inner tubular surface adapted to contact the limb and an outer tubular surface adapted to contact the fluid.

In accordance with more specific aspects of the present invention, the first end wall of the tank includes a limb-receiving aperture formed therein and the flexible tube includes first and second ends, the first end of the tube being secured to the periphery of the limb-receiving aperture in the first end wall, the second end of the tube secured to the second end wall. The second end of the tube is preferably connected to the second end wall of the tank at a position higher than that of the aperture in the first end wall, whereby a limb positioned in the tube will be elevated. The second end wall of the tank preferably includes a second aperture formed therein, the second end of the tube being secured to the periphery of the second aperture, the second aperture being formed in the second end wall at a position higher than that of the limb-receiving aperture in the first end wall.

In accordance with yet more specific aspects of the present invention, means are provided for securing the first and second ends of the tube to the apertures, the means preferably comprising a pair of ring-shaped members, one of each of which is disposed about the outer periphery of the apertures, respectively, the ends of the tubes positioned between the ring-shaped members and the outer periphery of the apertures, and means for securing the ring-shaped members to the end walls of the tank.

In accordance with other aspects of the present invention, the tank preferably includes means for draining the contents thereof which are positioned in the lower portion of the tank. Further, the first and second end walls of the tank each preferably have an elongated horizontal aperture near the top edges thereof for facilitating lifting of the tank by hand. The tank itself preferably comprises a substantially rectangular solid enclosure but open at the top, the tube extending through the middle of the tank lengthwise thereof between the opposed end walls at a height whereby the fluid placed in the tank is adapted to contact the entire exposed portion of the outer tubular surface to compress the tube radially inwardly about the limb placed therewithin.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF THE PREFERRED EMBODIMENT

Figure 1:
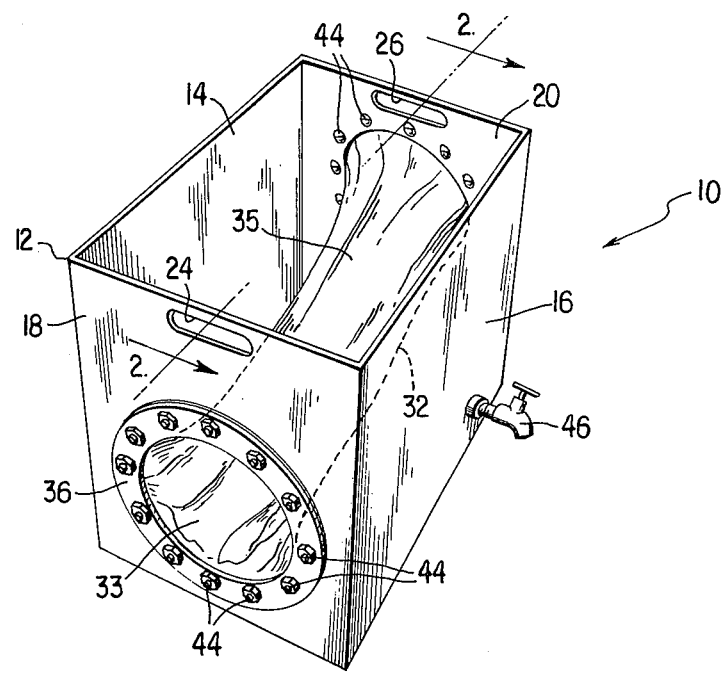
FIG. 1 is a perspective view of a preferred embodiment of the present invention prior to use.

Referring now to the drawings, wherein like reference numerals represent identical or corresponding parts throughout the several views, and, more particularly, to FIG. 1 thereof, a preferred embodiment of the limb compression and elevation apparatus of the present invention is indicated generally by reference numeral 10.

The apparatus 10 is seen to consist of a housing 12 in the form of a substantially rectangular solid tank which is open on the top. Tank 12 may be made of any durable, lightweight material, such as fiberglass.

In the preferred form, tank 12 includes substantially planar, opposing vertical side walls 14 and 16 which are connected at their ends by substantially planar, opposing vertical end walls 18 and 20. A bottom wall 22 connects the lower edges of side walls 14 and 16 and end walls 18 and 20 to form an enclosed tank which is adapted to receive a treatment fluid, such as hot or cold water therewithin.

Formed near the top edge of the end walls 18 and 20 are a pair of transversely elongated apertures 24 and 26 which act as hand grips for facilitating the portability of the tank 12.

Formed in the side wall 18, near its junction with bottom wall 22, is an aperture 28, which is illustrated as being substantially circular, although it will be understood that any suitable shape may be provided. A similarly sized aperture 30 is formed in the opposing side wall 20 hear the top edge thereof. It is noted that aperture 30 is positioned higher than aperture 28 in order to provide automatic elevation of the injured limb, in a manner which will be described in greater detail hereinafter.

Figure 2:
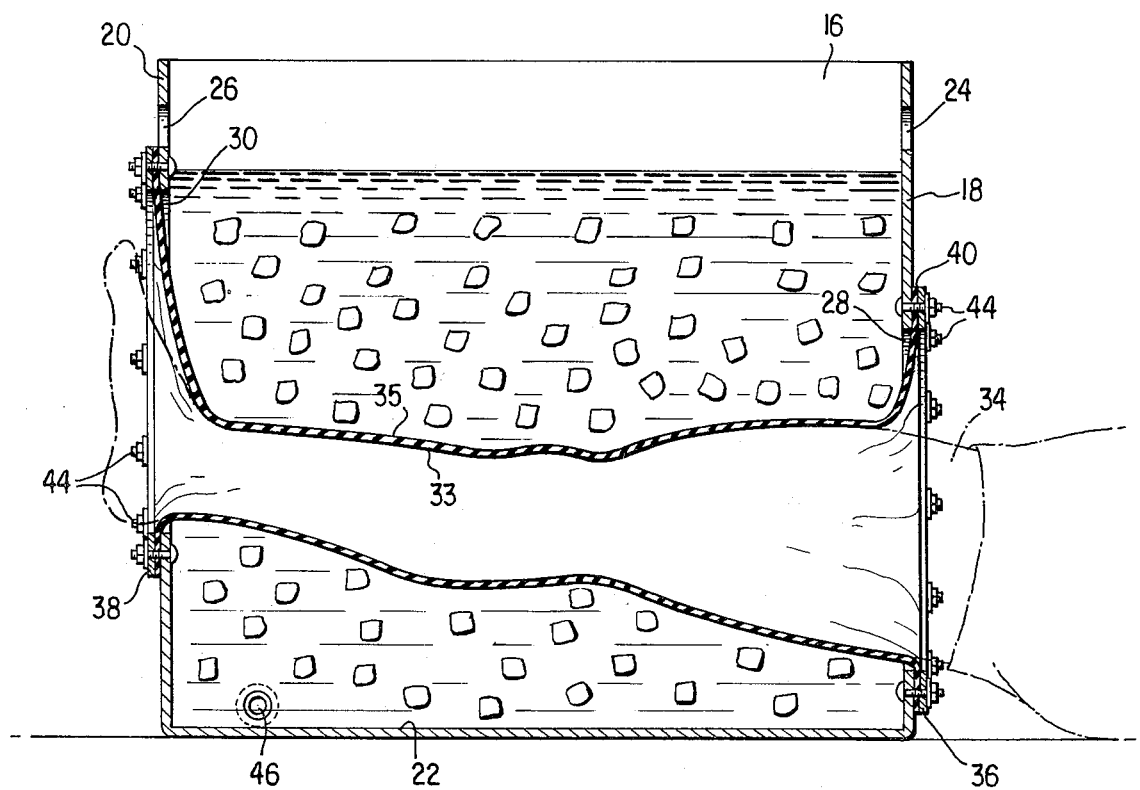
FIG. 2 is a longitudinal sectional view of the preferred embodiment illustrated in FIG. 1 and taken along line 2—2 thereof which illustrates the preferred embodiment during use.

Connected between the apertures 28 and 30 and extending longitudinally within the mid-portion of tank 12 is a flexible, fluid-impervious tubing 32 which includes an inner tubular surface indicated by reference numeral 33 and an outer tubular surface indicated by reference numeral 35. Tubing 32 may be formed of, for example, rubber, and functions as a sheath for receiving and encircling an injured limb, such as leg 32 (FIG. 2).

Tube 32 may be fastened to the periphery of apertures 28 and 30 by any suitable means. Provided in the preferred embodiment for this purpose are a pair of substantially circular ring members 36 and 38 which respectively hold the ends 40 and 42 of tube 32 against side walls 18 and 20 immediately adjacent the periphery of apertures 28 and 30, respectively.

Ring members 36 and 38 may be held in place by any suitable fastening means, such as nut and bolt assemblies 44. Fastening assemblies 44 are preferably distributed at close intervals about the ring members 36 and 38 to render the ends 40 and 42 of tube 32 fluid-tight. The extension of the ends 40 and 42 of tube 32 through the apertures 28 and 30, and their fastening in the manner indicated in FIG. 2, assists in providing a fluid-tight seal to prevent escape of fluid from within the tank.

A spigot 46 or similar fluid discharging device may be provided near the bottom of a side wall 16 to facilitate emptying of the tank 12, as desired.

In utilizing the apparatus of the present invention, if an athlete or any other person for that matter, sustains a soft-tissue injury to, for example, his knee, which can result in substantial swelling, the injured person immediately places his foot through the opening provided by aperture 28 in end wall 18 of tank 12. The injured party extends his foot through the inner tubular surface 33 of tube 32 until it exits through the opening 30 formed in opposite end wall 20. The tank 12 is then filled with an ice water mixture consisting of, for example, three-quarters tap water and one-quarter ice. The mixture may then be stirred to assure uniform contact with the entire exposed outer tubular surface 35 of tube 32. This results in an even cold compression being applied on the injured knee while the leg is maintained in an elevated position. One feature of the present invention is that it may easily be utilized on the football field or basketball court, requiring only a small amount of ice and water.

The present invention may also be utilized with hot water in heat treatment of the injured limb, which could be undertaken 2–3 days after cold treatment. Heat treatment could be utilized alone or in combination with cold treatment in what is known as "contrast therapy" (see the article by Gary K. Smith, supra). In contrast therapy, two tanks may be utilized, one having cold water and one having hot water. The tank with hot water would require occassional replinishment, or a thermoregulator may be used to keep the temperature hot.

A model constructed to verify the operation of the present invention consisted of a fiberglass tank of approximately 25½ inches long, 21 inches deep and 16½ inches wide. The apertures 28 and 30 were each approximately 9 inches in diameter. Aperture 28 was positioned approximately 2 inches from the bottom wall 22, while aperture 30 was positioned approximately 8 inches from bottom wall 22.

Obviously, numerous modifications and variations of the present invention are possible in light of the above teachings. It is therefore to be understood that within the scope of appended claims, the invention may be practiced otherwise than as specifically described herein.

I claim as my invention:

1. A device for treating an injured body limb, which comprises:

a tank adapted to contain a fluid and including first and second opposed end walls; and tubular means connected to and extending between said end walls of said tank for encircling and compressing said injured limb within the fluid contained in said tank, said tubular means comprising a liquid-impervious, flexible tube having an inner tubular surface adapted to contact said limb and an outer tubular surface adapted to contact said fluid; and wherein said first end wall of said tank includes a limb-receiving aperture formed therein and wherein said flexible tube includes first and second ends, said first end of said tube secured to the periphery of said limb-receiving aperture in said first end wall, said second end of said tube secured to said second end wall; and wherein said second end of said tube is connected to second end wall of said tank at a position higher than that of said aperture in said first end wall whereby a limb positioned in said tube will be elevated.

2. The device as set forth in claim 1, wherein said second end wall of said tank includes a second aperture formed therein, said second end of said tube being secured to the periphery of said second aperture, said second aperture being formed in said second end wall at a position higher than that of said limb-receiving aperture in said first end wall.

3. The device as set forth in claim 2, further comprising means for securing said first and second ends of said tube to said apertures, said means including a pair of ring-shaped members, one of each of which is disposed about the outer periphery of said apertures, respectively, said ends of said tube positioned between said ring-shaped members and said outer periphery of said apertures, and means for securing said ring-shaped members to said end walls.

4. The device as set forth in claim 1 or claim 2, wherein said tank includes means for draining the contents thereof positioned in the lower portion of said tank.

5. The device as set forth in claim 1 or claim 2, wherein said first and second end walls of said tank each include an elongated horizontal aperture near the top edges thereof for facilitating lifting of said tank by hand.

6. A device for treating an injured body limb, which comprises:

a tank adapted to contain a fluid and including first and second opposed end walls; and tubular means connected to and extending between said end walls of said tank for encircling and compressing said injured limb within the fluid contained in said tank, said tubular means comprising a liquid-impervious, flexible tube having an inner tubular surface adapted to contact said limb and an outer tubular surface adapted to contact said fluid; and wherein said tank comprises a substantially rectangular solid enclosure, but open at the top, said tube extending through the middle of said tank lengthwise thereof between said opposed end walls at a height whereby said fluid placed in said tank is adapted to contact the entire exposed portion of said outer tubular surface to compress said tube radially inwardly about said limb.

* * * * *